US012369648B2

(12) United States Patent
Moloney et al.

(10) Patent No.: US 12,369,648 B2
(45) Date of Patent: Jul. 29, 2025

(54) METHOD AND APPARATUS FOR AEROSOL PROVISION SYSTEM CONSUMABLE AUTHORIZATION

(71) Applicant: NICOVENTURES TRADING LIMITED, London (GB)

(72) Inventors: Patrick Moloney, London (GB); Anton Korus, London (GB); Justin Han Yang Chan, London (GB)

(73) Assignee: NICOVENTURES TRADING LIMITED, London (GB)

( * ) Notice: Subject to any disclaimer, the term of this patent is extended or adjusted under 35 U.S.C. 154(b) by 1309 days.

(21) Appl. No.: 15/733,689

(22) PCT Filed: Mar. 27, 2019

(86) PCT No.: PCT/GB2019/050877
§ 371 (c)(1),
(2) Date: Sep. 29, 2020

(87) PCT Pub. No.: WO2019/186158
PCT Pub. Date: Oct. 3, 2019

(65) Prior Publication Data
US 2021/0022407 A1    Jan. 28, 2021

(30) Foreign Application Priority Data
Mar. 29, 2018  (GB) .................................... 1805205

(51) Int. Cl.
*A24F 40/65*   (2020.01)
*A24F 40/53*   (2020.01)
(Continued)

(52) U.S. Cl.
CPC .............. *A24F 40/65* (2020.01); *A24F 40/53* (2020.01); *G05D 7/0617* (2013.01); *H04B 1/38* (2013.01); *H04L 63/101* (2013.01)

(58) Field of Classification Search
None
See application file for complete search history.

(56) References Cited

U.S. PATENT DOCUMENTS

| 2013/0284192 A1 | 10/2013 | Peleg et al. |
| 2014/0096781 A1 | 4/2014 | Sears et al. |

(Continued)

FOREIGN PATENT DOCUMENTS

| CN | 105308661 A | 2/2016 |
| CN | 105324044 A | 2/2016 |

(Continued)

OTHER PUBLICATIONS

"International Preliminary Report on Patentability received for PCT Patent Application No. PCT/GB2019/050877, mailed on Oct. 8, 2020", 8 pages.

(Continued)

*Primary Examiner* — Phu H Nguyen
(74) *Attorney, Agent, or Firm* — BURR & FORMAN LLP

(57) ABSTRACT

An aerosol provision device is configured to couple to a consumable component, and includes a transceiver configured for connection of the device to a communications network; and a processor configured to: obtain identification information from a consumable component engaged with the device, the identification information being uniquely provided to the consumable component or to a group of consumable components to which the consumable component belongs; configure the identification information as an identifier for the consumable component; send, via the communications network, an authorization query including the identifier to a remote server holding a list of one or more authorized identifiers; receive, via the communications network, an authorization response to the authorization query from the remote server; and identify the consumable com- (Continued)

ponent as authorized if the authorization response indicates that the identifier is comprised in the list of authorized identifiers.

19 Claims, 3 Drawing Sheets

(51) Int. Cl.
  *G05D 7/06* (2006.01)
  *H04B 1/38* (2015.01)
  *H04L 9/40* (2022.01)

(56) References Cited

U.S. PATENT DOCUMENTS

| | | |
|---|---|---|
| 2014/0096782 A1 | 4/2014 | Ampolini et al. |
| 2014/0322682 A1 | 10/2014 | Baym et al. |
| 2015/0181945 A1 | 7/2015 | Tremblay |
| 2015/0196057 A1 | 7/2015 | Wu |
| 2016/0174076 A1 | 6/2016 | Wu |
| 2016/0331027 A1 | 11/2016 | Cameron |
| 2016/0337362 A1 | 11/2016 | Cameron |
| 2016/0346489 A1 | 12/2016 | Finke et al. |
| 2016/0360789 A1 | 12/2016 | Hawes et al. |
| 2017/0020191 A1 | 1/2017 | Lamb et al. |
| 2018/0060873 A1 | 3/2018 | Chu |

FOREIGN PATENT DOCUMENTS

| | | | |
|---|---|---|---|
| CN | 105491898 A | | 4/2016 |
| CN | 105717812 A | | 6/2016 |
| CN | 106170218 A | | 11/2016 |
| CN | 106235414 A | | 12/2016 |
| CN | 106254143 A | | 12/2016 |
| CN | 107018490 A | | 8/2017 |
| EP | 2797448 A2 | | 11/2014 |
| EP | 3195739 A1 | | 7/2017 |
| EP | 3605952 A1 | | 2/2020 |
| RU | 2618436 C2 | | 5/2017 |
| WO | 2013098397 A2 | | 7/2013 |
| WO | 2013098398 A2 | | 7/2013 |
| WO | 2014150704 A2 | | 9/2014 |
| WO | 2015058531 A1 | | 4/2015 |
| WO | 2016023231 A1 | | 2/2016 |
| WO | 2017037457 A1 | | 3/2017 |
| WO | 2017124419 A1 | | 7/2017 |
| WO | 2017137510 A1 | | 8/2017 |
| WO | 2017205692 A1 | | 11/2017 |
| WO | 2018024154 A1 | | 2/2018 |

OTHER PUBLICATIONS

"International Search Report and Written Opinion received for PCT Patent Application No. PCT/GB2019/050877, mailed on Jun. 17, 2019", 11 pages.

"Notice of Allowance received for Chinese Patent Application No. 201980022777.9, mailed on Aug. 2, 2023", 6 pages (2 pages of English Translation and 4 pages of Official Copy).

"Notice of Allowance received for Korean Patent Application No. 2020-7027673, mailed on Aug. 1, 2023", 4 pages (1 page of English Translation and 3 pages of Official Copy).

"Office Action and Search Report received for Chinese Patent Application No. 201980022777.9, mailed on Feb. 12, 2023", 27 pages (10 pages of English Translation and 17 pages of Official Copy Only).

"Office Action received for European Patent Application No. 19716498.1 mailed on Aug. 12, 2022", 5 pages.

"Office Action received for Japanese Patent Application No. 2020-544514, mailed on Aug. 10, 2021", 8 pages (4 pages of English Translation and 4 pages of Official Copy).

"Office Action received For Russian Patent Application No. 2020131812, mailed on Mar. 1, 2021", 16 pages.

METHOD AND APPARATUS FOR AEROSOL PROVISION SYSTEM CONSUMABLE AUTHORIZATION

PRIORITY CLAIM

The present application is a National Phase entry of PCT Application No. PCT/GB2019/050877, filed Mar. 27, 2019, which claims priority from GB Patent Application No. 1805205.0, filed Mar. 29, 2018, each of which is hereby fully incorporated herein by reference.

TECHNICAL FIELD

The present disclosure relates to a method and apparatus for authorizing use of consumable components of aerosol provision systems.

BACKGROUND

Aerosol provision systems, such electronic cigarettes, that generate an inhalable vapor from one or more substrate materials, may comprise a main component that contains a power supply and operating electronics, and a cartridge containing the substrate material which is connectable to the main component to receive power therefrom for vapor generation. The main component, sometimes known simply as a device, can be reusable for multiple uses, via re-charging of the power supply for example. The cartridge may be designed as a disposable component in that when the substrate material has been used up, the cartridge is disconnected from the device and replaced by a new cartridge having a fresh supply of substrate material. The cartridge can therefore be considered as a consumable component.

Correct and safe operation of the system is important. A factor in this is the use of the device with appropriate consumables that are properly designed for that device. This can avoid, for example, supply of an incorrect power level to a consumable that might cause overheating or be inadequate to properly generate vapor.

Accordingly, approaches for enabling operation of aerosol provision devices with authorized consumable components are of interest.

SUMMARY

According to a first aspect of some embodiments described herein, there is provided an aerosol provision device configured to couple to a consumable component, and comprising: a transceiver configured for connection of the device to a communications network; and a processor configured to: obtain identification information from a consumable component engaged with the device, the identification information being uniquely provided to the consumable component or to a group of consumable components to which the consumable component belongs; configure the identification information as an identifier for the consumable component; send, via the communications network, an authorization query including the identifier to a remote server holding a list of one or more authorized identifiers; receive, via the communications network, an authorization response to the authorization query from the remote server; and identify the consumable component as authorized if the authorization response indicates that the identifier is comprised in the list of authorized identifiers.

According to a second aspect of some embodiments described herein, there is provided a method of operating an aerosol provision device configured to couple to a consumable component, the method comprising: detecting engagement of a consumable component to the device; obtaining identification information from a consumable component coupled to the device, the identification information being uniquely provided to the consumable component or to a group of consumable components to which the consumable component belongs; configuring the identification information as an identifier for the consumable component; sending, via a communications network, an authorization query including the identifier to a remote server holding a list of one or more authorized identifiers; receiving, via the communications network, an authorization response to the authorization query from the remote server; and identifying the consumable component as authorized if the authorization response indicates that the identifier is comprised in the list of authorized identifiers.

According to a third aspect of some embodiments described herein, there is provided a server for enabling operation of an aerosol provision device comprising: a transceiver configured for connection of the server to a communications network; memory storing a list of one or more authorized identifiers each comprising identification information unique to a consumable component or a group of consumable components and configured to engage with an aerosol provision device; and a processor configured to: receive from an aerosol provision device, via the communications network, an authorization query including an identifier; interrogate the list of authorized identifiers for the said identifier; and send to the aerosol provision device, via the communications network, an authorization response indicating that the said identifier is comprised in the list of authorized identifiers if the interrogation finds the said identifier in the list of authorized identifiers.

According to a fourth aspect of some embodiments described herein, there is provided a method of operating a server configured to enable operation of an aerosol provision device, the method comprising: storing in a memory a list of one or more authorized identifiers each comprising identification information unique to a consumable component or a group of consumable components and configured to engage with an aerosol provision device; receiving from an aerosol provision device, via the communications network, an authorization query including an identifier; interrogating the list of authorized identifiers for the said identifier; and sending to the aerosol provision device, via the communications network, an authorization response indicating that the said identifier is comprised in the list of authorized identifiers if the interrogation finds the said identifier in the list of authorized identifiers.

According to a fifth aspect of some embodiments described herein, there is provided a system comprising an aerosol provision device and a remote server for enabling operation of the aerosol provision device, in which: the aerosol provision device is configured to engage with a consumable component, and the device comprises: a transceiver configured for connection of the device to a communications network; and a processor configured to: obtain identification information from a consumable component engaged with the device, the identification information being uniquely provided to the consumable component or to a group of consumable components to which the consumable component belongs; configure the identification information as an identifier for the consumable component; send, via the communications network, an authorization query including the identifier to the remote server; receive, via the communications network, an authorization response to the authorization query from the remote server; and identify the consumable component as authorized if the authorization response indicates that the identifier is comprised in the list of authorized identifiers; and the server comprises: a transceiver configured for connection of the server to a communications network; memory storing a list of one or more authorized identifiers each comprising identification information unique to a consumable component or a group of consumable components and configured to engage with an aerosol provision device; and a processor configured to: receive from the aerosol provision device, via the communications network, an authorization query including an identifier; interrogate the list of authorized identifiers for the said identifier; and send to the aerosol provision device, via the communications network, an authorization response indicating that the said identifier is comprised in the list of authorized identifiers if the interrogation finds the said identifier in the list of authorized identifiers.

According to a sixth aspect of some embodiments described herein, there is provided a computer program for implementation on a processor comprised in an aerosol provision device, the computer program configured, when implemented by the processor, to enable the processor to perform a method according to the second aspect.

According to a seventh aspect of some embodiments described herein, there is provided a computer program for implementation of a processor comprised in a remote server, the computer program configured, when implemented by the processor, to enable the processor to perform a method according to the fourth aspect.

These and further aspects of the certain embodiments are set out in the appended independent and dependent claims. It will be appreciated that features of the dependent claims may be combined with each other and features of the independent claims in combinations other than those explicitly set out in the claims. Furthermore, the approach described herein is not restricted to specific embodiments such as set out below, but includes and contemplates any appropriate combinations of features presented herein. For example, a method or apparatus may be provided in accordance with approaches described herein which includes any one or more of the various features described below as appropriate.

BRIEF DESCRIPTION OF THE DRAWINGS

Various embodiments of the disclosure will now be described in detail by way of example only with reference to the following drawings in which.

DETAILED DESCRIPTION

Figure 1:
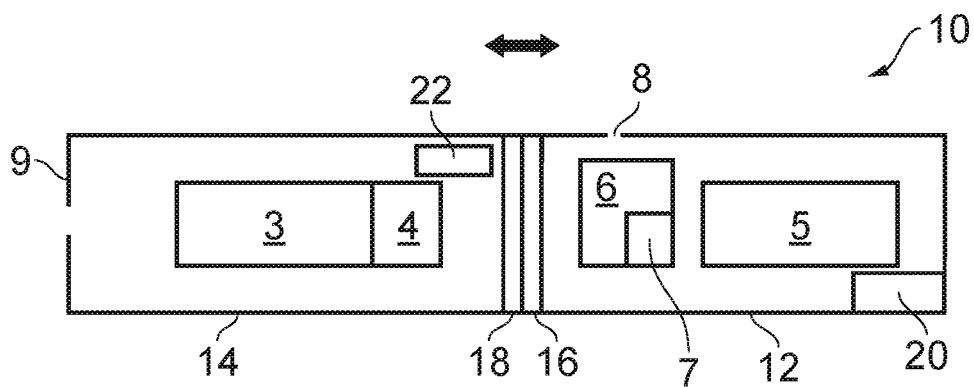
FIG. 1 shows a schematic representation of an example aerosol provision system with which examples of the present disclosure may be implemented.

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As used herein, the terms "vapor provision device/system", "electronic vapor provision device/system", "aerosol provision device/system", "electronic aerosol provision device/system" and similar terms are intended to include non-combustible aerosol and vapor provision systems (non-combustible smoking articles) such electronic smoking articles including electronic cigarettes or e-cigarettes that create vapor or aerosol from aerosolizable substrate materials by heating or other techniques such as vibration, heating devices that release compounds from substrate materials without burning such as tobacco heating products, and hybrid systems that generate aerosol from a combination of substrate materials, for example hybrid systems containing liquid or gel or solid substrates. The term "aerosol" may be used interchangeably with "vapor".

In some embodiments, the non-combustible aerosol or vapor provision system is a non-combustible smoking article such as an electronic cigarette, also known as a vaping device. The non-combustible aerosol provision system may comprise one or more components, such as a heater and an aerosolizable substrate. In some embodiments the system comprises a heater, a power supply capable of supplying power to the heater, an aerosolizable substrate such as a liquid or gel, a housing and optionally a mouthpiece. The aerosolizable substrate may be contained in a substrate container. The substrate container may be combined with or comprise the heater.

In some embodiments, the non-combustible aerosol or vapor provision system is a heating product which releases one or more compounds by heating, but not burning, a substrate material. The substrate material is an aerosolizable substrate material which may be, for example, tobacco or other non-tobacco products, which may or may not contain nicotine. In some embodiments, the product is a tobacco heating product. The tobacco heating product may comprise a heater, a power supply capable of supplying power to the heater, and an aerosolizable substrate such as a solid or gel material. The heating product may comprise an aerosolizable substrate such as a solid or gel material and a heat source which is capable of supplying heat energy to the aerosolizable substrate without any electronic means, such as by burning a combustion material, such as charcoal. The heating product may also comprise a filter capable of filtering the aerosol generated by heating the aerosolizable substrate.

In some embodiments, the non-combustible aerosol or vapor provision system is a hybrid system for generating aerosol by heating, but not burning, a combination of substrate materials. The substrate materials may comprise for example solid, liquid or gel which may or may not contain nicotine. In some embodiments, the hybrid system comprises a liquid or gel substrate and a solid substrate. The solid substrate may be, for example, tobacco or non-tobacco products, which may or may not contain nicotine. In some embodiments, the hybrid system comprises a liquid or gel substrate and tobacco.

The aerosol or vapor may be produced or released from a variety of substrates in various ways depending on the nature of the device, system or product. These include heating to cause evaporation, heating to release compounds, and vibration of a liquid or gel to create droplets. The substrate material, which may be one or more different materials within one system, may generally be referred to as an aerosol forming substrate, an aerosol forming substrate material, an aerosolizable substrate, an aerosolizable substrate material, or similar term. The substrate material may be a solid, a liquid or a gel, and may or may not comprise or include tobacco, and may or may not produce an aerosol or vapor containing nicotine. For example, the aerosolizable substrate material may comprise a vapor or aerosol generating agent or a humectant, such as glycerol, propylene glycol, triacetin or diethylene glycol.

In particular, embodiments of the disclosure are concerned with systems comprising two separable components that are connected together in use, namely a device component that may be reusable and a consumable component that may be disposable or single use and which may contain aerosolizable substrate material.

FIG. 1 shows a highly schematic diagram (not to scale) of an example aerosol/vapor provision system such as an e-cigarette 10. The e-cigarette has a generally elongate shape comprising two main components, namely a control or power component, section or unit 12, and a cartridge assembly or section 14, that operates as an aerosol generating component. In this example, the components are arranged end-to-end, but other arrangements are possible, such as a side-by-side arrangement. Also, the overall shape of the system need not be elongate.

The control or power component 12 may be referred to as a "device", and is typically configured to be reusable (although this is not essential) to provide a plurality of aerosol provision experiences to a user over a period of days, weeks, months or years. The cartridge assembly 14, which in some designs of system may be termed a "cartomizer", contains aerosolizable substrate material and is typically intended to be replaced when the substrate material has been used up, or consumed. Hence, this component 14 may be referred to as a "consumable component". In some examples, however, the consumable component may be configured to be refilled with substrate material when a first amount of substrate material has been consumed. The consumable component 14 may be intended to be replaced when other parts that may be contained within it reach an end of an operational lifetime, such as a heating element or a wicking component. In many examples, a single device will be able to be used with a plurality of consumable components which are replaced in sequence. In such a case, the operational lifetime of the device is intended to be longer than the operational lifetime of the consumable component. This is not essential, however, and the device may also be designed as a replaceable part, with a relatively short operational lifetime. In the following description, consumable components will mainly be described as containing aerosolizable substrate material, but as is clear from above, the disclosure is not limited in this way, and a consumable component may have a reservoir or other receiving area which can be supplied with aerosolizable substrate material, or may be consumable with respect to a heater, a wick or other parts.

The consumable component 14 includes a portion or portions of aerosolizable substrate material 3 which may be one or more of a liquid or gel stored in a reservoir or other storage volume, a gel portion on a support, or a solid material, which may or may not be or include tobacco material. The substrate material is material from which an aerosol is to be generated, which may or may not be an aerosol containing nicotine. One or more flavorants may be included in liquid, gel or solid form. The consumable component 14 also comprises an atomizer (vaporizer) 4 operable to generate aerosol from the substrate material 3. The nature of the atomizer 4 will be appropriate to the format of the substrate material 3. Examples include an electrical heating element to which liquid substrate material is delivered by a wicking, capillary or other liquid transport arrangement for the liquid to be vaporized, a vibrating perforate sheet to which liquid is delivered for droplet generation, and an electrical heater to apply heat to a solid substrate material to release volatiles. A wide variety of vaporizer or atomizer configurations or assemblies able to generate vapor from aerosolizable substrate material delivered to or otherwise associated with the atomizer are known or will be readily apparent to the skilled person, and the present disclosure is not limited in this regard. Embodiments of the disclosure are applicable to all and any such assembly configurations. Also, in some examples one or more parts of the atomizer 4 may be located in the device 12 instead of the consumable component 14.

The consumable component 14 also includes a mouthpiece 9 having an opening or air outlet through which a user may inhale the aerosol generated by the vaporizer 4.

The device 12 provides power and control for generation of aerosol by the atomizer 4 from the aerosolizable substrate material 3. Hence, the device includes a cell or battery 5 (referred to herein after as a battery, and which may be re-chargeable) to provide power for electrical components of the e-cigarette 10, such as the atomizer 4. Additionally, there is a controller 6 such as a printed circuit board and/or other electronics or circuitry for generally controlling the e-cigarette. The controller 6 includes (or may be) a processor 7 (a microprocessor executing software, or electronics configured to perform the functions of the processor as described herein). The controller 6 connects the atomizer 4 to the battery 5 when vapor is required, for example in response to a signal from an air pressure sensor or air flow sensor (not shown) that detects an inhalation on the system 10 during which air enters through one or more air inlets 8 in a wall of the housing of the device 20 (or a wall of the consumable component 14 in other examples). When the atomizer 4 receives power from the battery 5, the atomizer 4 operates to generate aerosol from the aerosolizable substrate material 3, and this is then inhaled by a user through the opening in the mouthpiece 9. The aerosol is carried from the atomizer 4 to the mouthpiece 9 along an air channel (not shown) that connects the air inlet 8 to the atomizer 4 to the air outlet when a user inhales on the mouthpiece 9. Over time, the aerosolizable substrate material is consumed, in that the entirety of a liquid or gel is evaporated, or all available volatiles are released from a solid or gel, or the substrate material is in some other way exhausted so that generation of aerosol is no longer possible, or no longer desirable if the available quality of achievable aerosol is below an acceptable level. When this happens, the consumable component can be considered to have been consumed. A new portion of aerosolizable substrate material is required.

The device 12 also comprises a transceiver 20 configured to enable the device 12 to be connected to a communications network, and to send and receive data and messages to external or remote entities using the network. The network may be configured as a wired network, a wireless network, or a combination of wired and wireless. It may be the internet, or a local area network, a wide area network, or a radio telecommunications network, for example. The transceiver 20 can be configured according to the intended network arrangement, and may be a radio frequency transmitter and receiver, or may be configured as a port or socket for connection of a cable (such as USB or Ethernet) so that the device can be connected to a wired network, or to make a physical connection to a local entity such as a mobile telephone or personal computer that is able to continue the network more widely, such as by Wi-Fi connection to the internet or a radio connection to a telecommunications network. The transceiver may be a Bluetooth® transceiver for similar connection to a local entity of the user. The disclosure is not limited with regard to the format of the transceiver 20 and the nature of the communications network to which the device 12 can be connected, and the skilled person will appreciate that a variety of alternatives can be used as convenient. The disclosure relates to communication between the device and a remote server, and as will be apparent from the foregoing, this communication may be direct between the device and the server, or indirect via one or more intermediate entities.

The device 12 and the consumable component 14 are separate connectable sections detachable from one another by separation in a direction parallel to the longitudinal axis (in this example), as indicated by the solid arrow in FIG. 1. The components 12, 14 are joined together when the device 10 is in use by cooperating engagement elements 16, 18 (for example, a screw or bayonet fitting) which provide mechanical and electrical connectivity between the device 12 and the consumable component 14. This is merely an example arrangement, however, and the various elements may be differently distributed between the device 12 and the consumable component 14, and other parts and elements may be included. The two sections may connect together for use end-to-end in a longitudinal configuration as in FIG. 1, or in a different configuration such as a parallel, side-by-side arrangement. The system may or may not be generally cylindrical and/or have a generally longitudinal shape. Either or both sections or components 12, 14 may be intended to be disposed of and replaced when exhausted (the reservoir is empty or the battery is flat, for example), or be intended for multiple uses enabled by actions such as refilling the reservoir and recharging the battery. Embodiments and examples of the present disclosure are applicable to any of these configurations and other configurations of which the skilled person will be aware.

Figure 2:
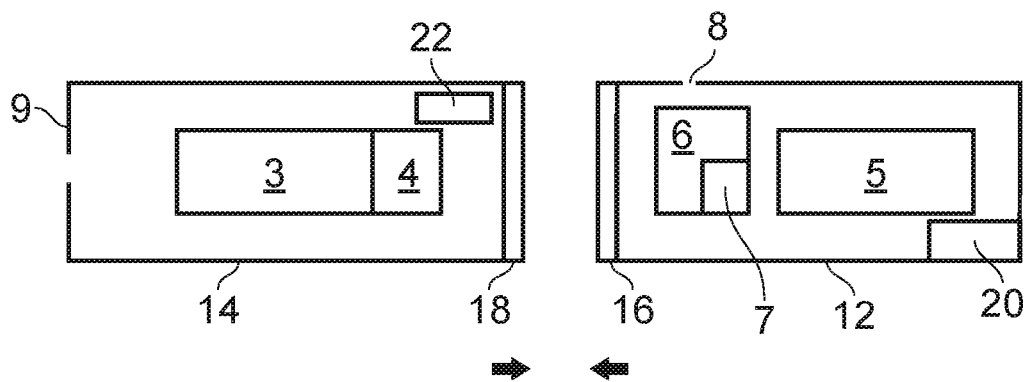
FIG. 2 shows a schematic representation of the example aerosol provision system of FIG. 1 in a separated condition.

FIG. 2 shows a schematic representation of the electronic cigarette 10 of FIG. 1 in an uncoupled arrangement, in which the device 12 is separate from the consumable component 14, and these two sections are ready to be coupled, engaged or connected together for aerosol provision.

As noted above, the device 12 can be operated with a series of consumable components 14. However, it can be useful to determine the nature or identity of any given consumable component 14 that has been connected to the device 12, so that the device can be appropriately operated to control the consumable component 14 correctly having regard to characteristics of the consumable component 14, or prevented from operating if desired. For example, a range of consumable components 14 might be made available that offer different flavors or nicotine strengths from the aerosolizable substrate material 3. The different aerosolizable substrate materials may require different levels or patterns of electrical power to be supplied from the battery 5 to the atomizer 4, under control of the controller 6. More generally, there may be a maximum power level that is appropriate for a given aerosolizable substrate material or a given atomizer, so that the device should not over-supply power when operating with a consumable component with that characteristic. It can be desirable to inhibit the use of a device 12 with consumable components from third party sources that may have unknown characteristics, to ensure that the aerosol provision system 10 can be operated safely. Operation may also be undesirable with consumable components that have exceeded their shelf-life, or if some manufacturing defect is detected after a batch of consumable components has been placed on the market, or if re-use of a consumable component designed for single use is attempted. Other situations in which it is desirable to allow or prevent operation of a device with any given consumable will also be apparent to the skilled person, and the disclosure is not limited in this regard.

Accordingly, it is proposed that the consumable component be provided with identification information or an identifier that can be read or otherwise obtained or extracted from the consumable component by the device when the two are connected, engaged or coupled together by a user. The device then utilizes its transceiver to send the identifier over the communications network to a server entity which is able to ascertain if the identifier is included in a list of identifiers that are authorized or otherwise approved for use with the device. If the identifier is included in the list, the server notifies the device of this, and the device is then enabled to activate operation with the consumable component. This may include provision of appropriate power levels and timings if the identifier indicates relevant characteristics of the consumable component. In the event that the device is not able to verify that the identifier appears on the list of approved identifiers, for example if the server notifies the device of this, or if no notification with a positive approval is received by the device, the device can be prevented from operating with the consumable component. Hence, it is possible to determine, identify, verify or authenticate that any consumable component is recognized, authorized or approved for use with a given device.

The consumable component 14 is therefore provided with identification information 22 that can be obtained from the consumable component 14 by the device 12 when the two sections 12, 14 are connected together via the engagement elements 16, 18. The identification information may be unique to every individual consumable component. Alternatively, it may be unique to a group of consumable components. For example, the same identification information may be allocated to consumable components of the same model, such as all consumable components with a particular flavor or strength of aerosolizable substrate material. Alternatively, all consumable components in a particular production batch, or which were manufactured within a particular period of time, or by a particular manufacturer, or which are to be shipped to or from a particular geographical region or to a particular distribution or sales entity, may be given the same identification information.

The identification information may be provided in any format that is suitable to be obtained, read or otherwise extracted by the device 12, and then sent to a server entity. Many configurations are possible. In some examples, the consumable component is able to actively send the identification information 22 to the device 12 when the two sections are first coupled or engaged together (a "push" arrangement). In other examples, the consumable component 14 is passive and the device 12 operates independently to access the consumable component to obtain the identification information 22 (a "pull" arrangement). In still other examples, the device 12 can send a request or message to the consumable component 14, which sends the identification information 22 in response. In arrangements where action is required from the consumable component 14, it may be supplied with electrical power for the purpose from the device via the engagement elements 16, 18, or it may comprise its own power supply.

Examples of how to provide and obtain the identification information 22 are many and varied. The consumable component 14 may include one or more electrical components within a circuit accessible by the device 12 and which can take different physical values. The components may be resistors or capacitors, for example, and the device 12 accesses the circuit to obtain the value or values of the electrical component (such as by measuring current flow through a component or voltage drop across it), which is the identification information 22. Different electrical components can be placed in the circuit to given different identification information 22 to different consumable components.

Alternatively, the consumable component 14 might have a barcode, a QR code or similar optically readable code placed on a surface which is optically accessible to the device 12 either before or after the two components are engaged or coupled together. The device is provided with an optical source such as a laser or a light emitting diode configured to scan the code. The data extracted from the code is the identification information 22.

In another alternative, the consumable component 14 is provided with a memory or other data storage arrangement in which the identification information 22 is stored as data. The memory can be accessible by the device 12 so that the device 12 reads the identification information 22 directly. Alternatively, the consumable component 14 can be configured to extract the identification information 22 from the memory and send it to the device 12, either in response to a request from the device 12 or in response to a connection being made between the device 12 and the consumable component 14.

Other options for including identification information in the consumable component 14 will be apparent, and the disclosure is not limited in this regard. Regardless of the implementation, the identification information from the consumable component 14 is made available at the controller 6/processor 7 of the device 12.

Once the identification information 22 has been obtained by the device and is available at the processor 7, the processor 7 acts to configure the identification information 22 as an identifier to be used in an authorization exchange with a server entity. In some examples, the identification information 22 will already be in a useful format for an identifier, so the configuration is simply adopting the identification information 22 directly for use as an identifier. This may be the case if an optically readable code or a storage memory has been used to embed the identification information 22 in the consumable component 14, for example.

In other situations, it may be desirable for the processor to carry out some kind of conversion or other processing on the identification information 22 to produce an identifier of a suitable format for the intended authorization procedure. A pair of voltage values read from resistors in the consumable component 14 will likely need to be adapted into a single identifier, for example. The processor may be programmed with a suitable mathematical formula to convert electrical values or other identification information into an identifier, or the device may have a look-up table (or be able to access a look-up table via the network) that maps electrical values or other identification information onto identifiers so the processor can extract the corresponding identifier. To account for tolerances in the values of electrical components and errors in measuring voltage and current, or other inexactitudes in encoding or obtaining the identification information, a range of obtained identification information values may be set to correspond to a single identifier.

The identifier, which may be a numerical value or a data string, for example, may be used directly in the authorization procedure if its format is suitable, or may be encoded or adapted in some way to make it suitable for inclusion in a message for sending via a communications network. In the following description, language indicating that the identifier is "included" or "comprised" in a message, query, response, list or the like is intended to cover both alternatives.

Figure 3:
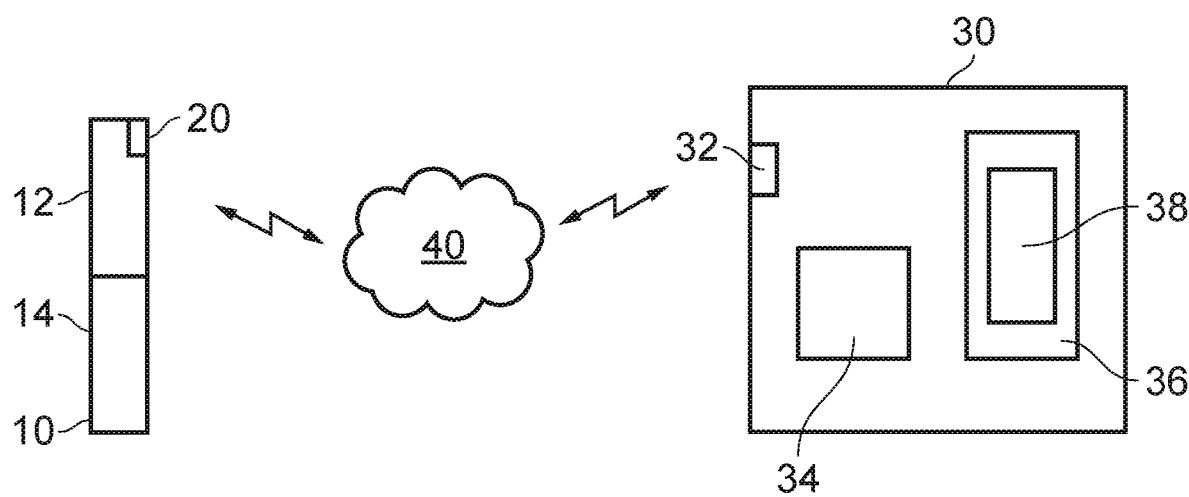
FIG. 3 shows a schematic representation of a system for enabling authorization of a consumable component according to examples of the present disclosure.

FIG. 3 shows a simplified schematic representation (not to scale) of a system for enabling operation of an aerosol provision device by use of such an identifier. The system comprises an aerosol provision system 10 such as that shown in FIG. 1, and comprising a device 12 coupled to a consumable component 14, and a remote server 30. The device 12 of the aerosol provision system 10 and the remote server 30 are able to communicate using a communications network 40. The network 40 is illustrated as being wireless for clarity, but may be wholly or partly wired as noted above. One or more intermediate entities may be involved in passing messages between the device 12 and the server 30 via the network 40; again, these are not shown for clarity. In other words, the connection between the device 12 and the server 30 may be direct or indirect.

The server 30 is remote from the aerosol provision device 10, in that the network is utilized to enable the two entities to communicate. The server 30 is able to receive messages from and send messages to a plurality of aerosol provision devices so that authorization of multiple aerosol provision systems for users in multiple locations is enabled. The server 30 comprises a transceiver or communications interface 32 for connection with the network 40 to enable the receipt and transmission of messages; this can take any format as preferred. Also included is a processor 34 for executing software to implement an authorization procedure. The server 30, in this example, also includes memory (data storage) 36 in which is stored or held a list 38 of identifiers of authorized consumable components 14. The list can be maintained in an up-to-date condition as discussed later.

The list 38 can be stored in memory 36 comprised within the server 30 as illustrated. Alternatively, the list 38 can be held in memory that is separate (at a proximate or remote location) from the server 30, where the processor 34 is able to access the list 38, by using the network 40, or by a local network or a wired connection, for example. Accordingly, where the list 38 is described as being "held" by the server 30 (or similar language), this is intended to cover arrangements both where the server holds access to the list 38 by the list 38 being maintained within the server 30, and arrangements where the list is separate from but accessible by the server 30. Also, the system may comprise more than one server and/or memory and/or list.

FIG. 4 shows a flow chart of a method for enabling use of a consumable component with an aerosol provision device using an identifier.

In S1, a user couples a device to a consumable component, as described above. In S2, the device, using its processor, obtains from the consumable component identification information which is unique to that consumable component or to a group of consumable components to which the present consumable component belongs. Options for providing the consumable component with identification information and for the device to acquire the identification information are described above. In a third step, S3, the device configures the identification information as an identifier, which is again unique to the consumable component or to a group to which the consumable component belongs. The identifier therefore identifies the consumable component or a group, batch or type of consumable component. Options for configuring the identifier have been described.

The method moves to S4, in which the processor of the device takes the identifier and formulates a message containing the identifier, where the message is an authorization query to enquire whether the identifier identifies an authorized consumable component. The message can take any format that is able to be understood by the remote server as an authorization query. The device sends the authorization query containing the identifier to the server, and the server receives the authorization query in S5.

In S6, the server accesses its held list of authorized identifiers (where as noted above, the list may be in memory comprised in the server, or in separate memory accessible by the server), and interrogates or otherwise searches the list for the identifier in the authorization query. Next, S7 is a query step to determine if the identifier has been found in the list.

If the answer to the S7 query is yes, indicating that the identifier is on the held list of authorized identifiers, the method moves to S8*a*, in which the server formulates a message for the device, and sends it to the device via the network in reply to the authorization query. The message is an authorization response, which is a positive authorization response which indicates that the identifier appears on the list. The message can take any format that is able to be understood by the device as a positive response. It does not need to include the identifier, but the identifier may be included as a clarification or check that the authorization query and the authorization response have been sent and received without error, so that the correct identifier has been verified. Excluding the identifier from the message simplifies the generation of the message and may reduce the amount of data to be transmitted, however.

In S9*a*, the positive authorization response is received by the device. This informs the processor of the device that the consumable component is authorized, so that in S10*a* the processor activates or enables the device for operation with the consumable component. Aerosol can then be generated by the aerosol provision system from the aerosolizable substrate material in the consumable component when required by the user, such as in response to an inhalation or manipulation of a switch or button. This operation, following a positive authorization response, can be considered to be an authorized activation.

If the answer to the S7 query is no, indicating that the identifier is not on the held list of authorized identifiers, the method can follow one of two alternatives. In a first alternative, in 8*b* the server formulates and sends a negative authorization response to the device, in reply to the authorization query. As with the positive authorization response, any suitable message format may be used, and the message may or may not include the identifier.

In S9*b*, the negative authorization response is received by the device. This informs the processor of the device that the consumable component is not authorized. Hence, in 10*b*, the processor does not activate or enable the device for operation with the consumable component. The aerosol provision system is therefore not operable to generate aerosol, and the user will need to swap the consumable component for a new consumable component, which will be verified for authorization following the same method.

Alternatively, on receipt of the negative authorization response, the processor may activate or enable the device for operation with the consumable component in a more conservative manner than when a positive authorization response is received (such as for safety reasons). For example, it may be desirable to reduce the amount of heating to avoid potential disassociation of certain aerosolizable substrate materials that might be present in the consumable component. However, this reduced amount of heating may also produce less vapor. This can be contrasted with operation of the device in the context of a positive authorization response, where a higher level of heating might be employed if this is known to be compatible with aerosolizable substrate material in the identified consumable component. In this context, having a recognised identifier allows operation of the device to be optimized to the properties of the identified consumable component, for example in terms of an amount of heating and vapor production. In contrast, the absence of a recognized identifier may lead to the use of default operation such as adopting a lowest common denominator or generic approach in order to help compatibility with an unidentified consumable component. This is turn may lead to sub-optimal operation compared to having a recognized identifier, but might be more attractive for a user than preventing operation of the device altogether.

In a second alternative, in 8*c*, the server does nothing following the null result of the authorization list interrogation in S7, so no authorization response is sent to the device. Hence, in 9*c*, the device notes that no authorization response has been received, perhaps after a predetermined period of time allowed for an authorization response has elapsed. Then, as in 10*b*, in 10*c*, the processor does not active or enable the device for operation with the consumable component.

Following the example method of FIG. 4, it is only possible for the user to use his aerosol provision device after adding a new consumable component if a positive authorization response is obtained from the server. If no authorization response is obtained, the device is not activated for operation with the consumable component and the user is not able to use the aerosol provision device. However, the condition of no positive authorization response being received by the device may not be a consequence of the server not finding the identifier on the list of authorized identifiers. Other conditions and circumstances can produce the same situation, so it may not be desirable to interpret an absence of any positive authorization response only as an indication that the consumable component is unauthorized. This interpretation can prevent a user from using a consumable component which is authorized, but which is not possible at the current time to verify as being authorized.

Accordingly, examples of the method include procedures for allowing unauthorized activations of the device for use with one or more consumable components in situations where it is not possible to ascertain whether or not a consumable component is included in the list of authorized consumable components held at the server. Note that it is the activation of the device which is unauthorized, and not the consumable component. At the time of activating the device, the status of the consumable component is not known.

There are a number of situations in which verifying whether a consumable component is authorized may not be possible. For example, the communications network may be inoperable, or may be inaccessible by the device, such as if the device uses radio telecommunication and is in an area of poor telecommunications network coverage. The device may have insufficient battery power available to formulate and transmit the authorization query or receive a response. The server may be temporarily unavailable, such as if it is taken "off line" for maintenance, or is experiencing a high volume of authorization queries and is not able to process them all. Other such circumstances will be readily apparent. In general, the circumstances will be some kind of suspension or failure of operation of one or more elements involved in the processing and exchange of messages between the device and the server.

In many such cases, the processor of the device will be able to determine that a circumstance has arisen that will make it unable to obtain an authorization response from the server, and be able to distinguish this from an absence of any authorization response from the server when one is expected following the successful transmission of an authorization query. For example, the device can be configured to detect a failure in the network that will prevent the sending and receiving of messages between the device and the server. In another case, the server may be configured to send a message to the device indicating that it is not currently available or able to respond to an authorization query.

When the device notes that there is some reason that means it will not be able to obtain an authorization response from the server when a new consumable cartridge has been connected, the processor of the device can be configured to allow an unauthorized activation of the device for operation with that consumable cartridge. The user is therefore not precluding from using the aerosol provision system just because of a network or server failure or similar circumstance that prevents the authorization procedure from being carried out.

The processor of the device may be configured such that, if an unauthorized activation is enabled, a further attempt is made to communicate with the server to obtain an authorization response after a relatively short time period, such as one minute, five minutes, ten minutes, 30 minutes, one hour, or two hours. This might continue at regular intervals until an authorization response is obtained for the consumable component.

Figure 4:
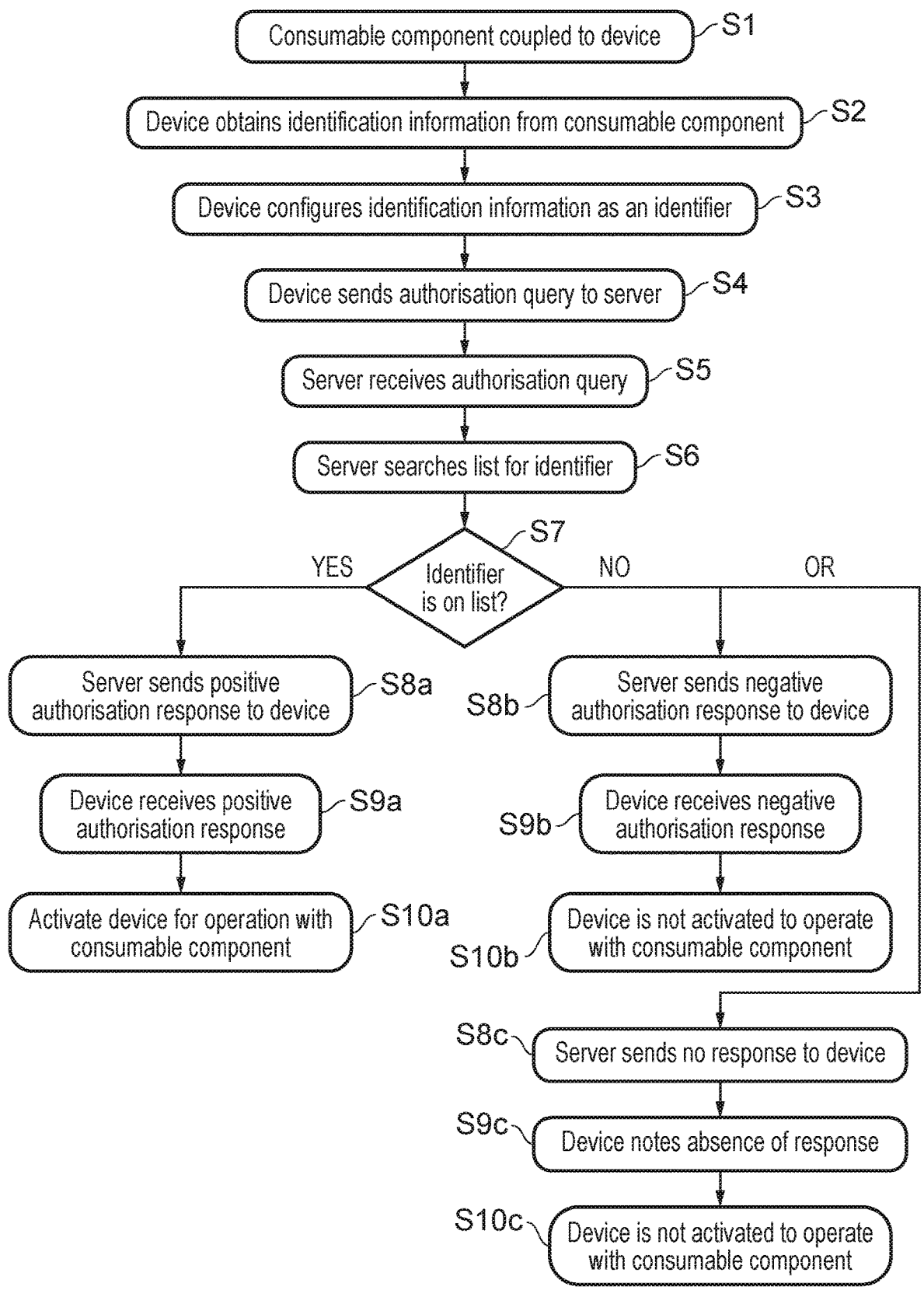
FIG. 4 shows a flow chart of an example method of consumable component authorization according to the present disclosure.

It may be considered undesirable to allow unauthorized activations to continue indefinitely, however. Accordingly, the processor of the device may be programmed (or otherwise provided such as by a message sent from a remote entity) with a maximum allowable number of unauthorized activations, and configured to maintain a count of the number of unauthorized activations which have been enabled. When the number of enabled unauthorized activations equals the maximum allowable number, no further unauthorized activations are permitted. Hence, if a new consumable component is engaged with the device and the device determines that there is an inability to obtain an authorization response, an unauthorized activation is only enabled if the number of previous unauthorized activations plus the current unauthorized activation is less than or equal to the predetermined maximum allowable number of unauthorized activations. The maximum allowable number of unauthorized activations may be set to be only one, or may be a small number such as three, five or ten. Other numbers or larger numbers may also be chosen.

When the count of unauthorized activations reaches the predetermined number, the processor will not enable further unauthorized activations. This may be a permanent condition. However, to prolong the utility of the device, a reset of the count of unauthorized activations may be implemented. For example, a predetermined period of time may be set in the processor such the amount of elapsed time since the final allowable unauthorized activation is measured, and when this reaches the set predetermined period of time, the count of unauthorized activations is set back to zero, or otherwise reduced below the predetermined maximum allowable number. The device is thereby enabled to implement more unauthorized activations in the future. The period of time may be set to be any convenient duration, such one day, three days, one week, two weeks or a month. Other, shorter or longer amounts of time may also be chosen. Also, counts of other operations made by the device or system may be maintained to achieve a reset, in alternative configurations. For example, the processor may keep a count of the number of authorized activations which have been performed since the final allowable unauthorized activation, and when this count has reached a preset quantity, the count of unauthorized activations is set back to zero or to a reduced number. Hence, the processor may be configured to allow more unauthorized activations when ten or 15 or 20 or some other number of authorized activations have been carried out. The number of allowable unauthorized activations may be set up as a proportion of the number of authorized activations. For example, the processor may allow two unauthorized activations for every ten authorized activations. Other values for these numbers may be employed as preferred.

Alternatively or additionally, the processor may be configured such that the count of unauthorized activations can be reset in response to a message received by the device via the network, such as from the server. The message is a permission message, indicating that further unauthorized activations are permitted for that device. The permission message can be initiated, for example, by the user communicating with a third party approved operator (by telephone, email, SMS or social media messaging or the like) to request re-enablement of his device for unauthorized activations. The operator can arrange for the server to send the permission message, or it may be sent from another entity via the network. Alternatively, the operator may issue a re-enablement code or message to the user that the user communicates to the device, such by as connecting the device to a mobile telephone and entering the code into the telephone or connecting the telephone to a URL provided by the operator which downloads a re-set signal to the telephone and hence to the device.

In some examples, the server or another entity may send a message to a device to reset, reduce, increase or otherwise alter the number of allowable unauthorized activations other than in response to a user request.

From the foregoing description, it will be appreciated that a range of conditions to enable resetting of the count of unauthorized activations is contemplated. The condition may be internally monitored by the device, so that the device can reset the count once the condition is met. Otherwise, the condition may be receipt of a message or other instruction from an external entity, which gives the device permission to reset the count. Two or more conditions can be utilized by a single device. They may operate in parallel so that the condition which is met first allows the reset, or two or more conditions may all need to be met to allow the reset, or the conditions may run in series so that a first condition being met then triggers the operation of a second condition which must also be met.

FIG. 5 shows a flow chart of steps in an example method for allowing and managing unauthorized activations of the device with a consumable component in the event that an authorization response cannot be obtained.

In S11, the processor recognizes that there is some inability preventing it from being able to obtain an authorization response for a particular consumable component. This may occur during, before or after any of S1 to S9a/9b/9c of the method of FIG. 4, for example, for any of the reasons noted above such as failure of the communications network. Once such an inability has been noted, the processor, in S12, determines (such as by retrieving from memory) a count of any previous unauthorized device activations, which may be designated as a numerical value n. In S13, the processor tests to see if a value of n+1, reflecting the number of previous unauthorized activations plus the current potential unauthorized activation for the current consumable component, is less than or equal to a value N which is a predetermined number of allowable unauthorized activations permitted to the device. If n+1≤N, the test of S13 is answered in the affirmative and the method proceeds to S14a in which the device is activated to operate with the consumable component in an unauthorized activation. In S15a, the processor increases the count n to n+1 to reflect the new total number of unauthorized activations that occurred. Alternatively, S13 could be a test to determine if n<N. If the number of previous unauthorized activations is less than the predetermined maximum number of allowable unauthorized activations, there must be at least one more allowable unauthorized activation still available, so S13 can be answered in the affirmative.

If the test of S13 has a negative result, this indicates that the permitted total number of unauthorized activations has already been carried out, and no further unauthorized activations are allowed. Hence, in S14b, the device is prevented from activating for operation with the consumable component. Only authorized activations can be carried out going forward, such as by following S1 to S10a of the FIG. 4 method.

Figure 5:
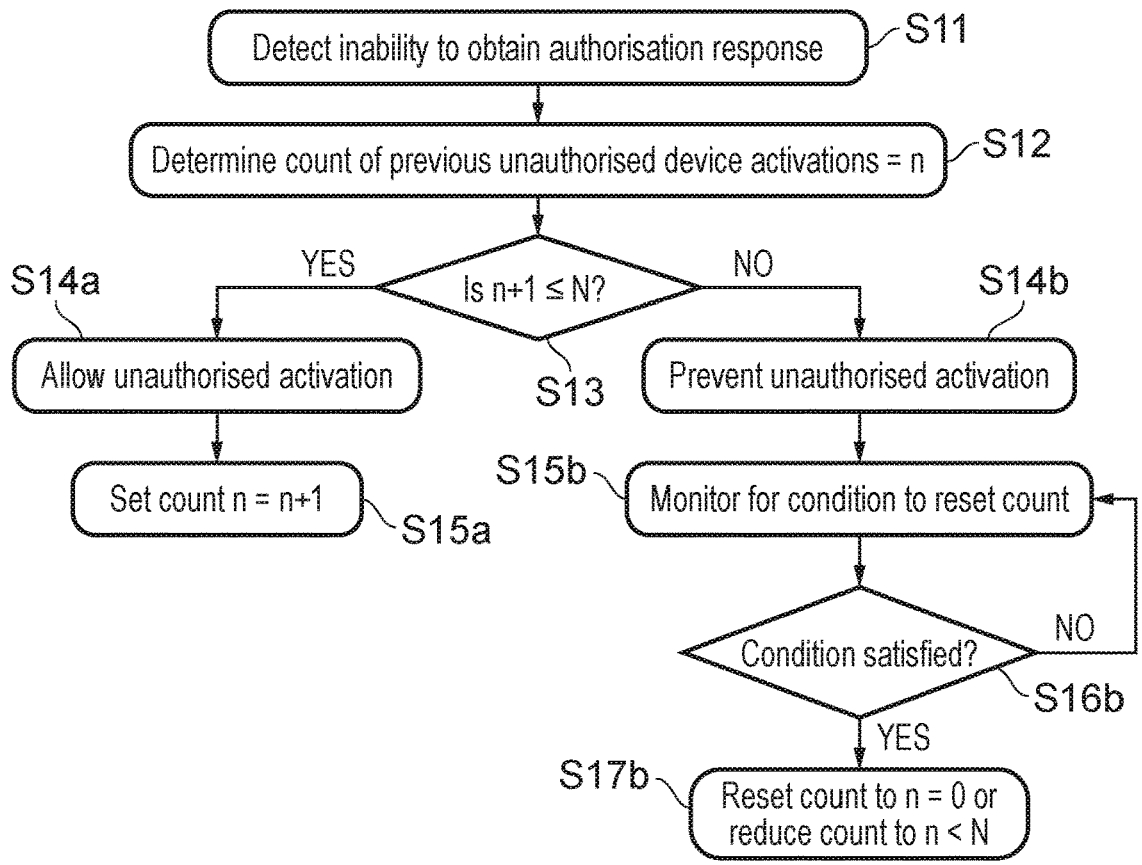
FIG. 5 shows a flow chart of an example method for managing unauthorized activations of an aerosol provision system according to the present disclosure.
Figure 6:
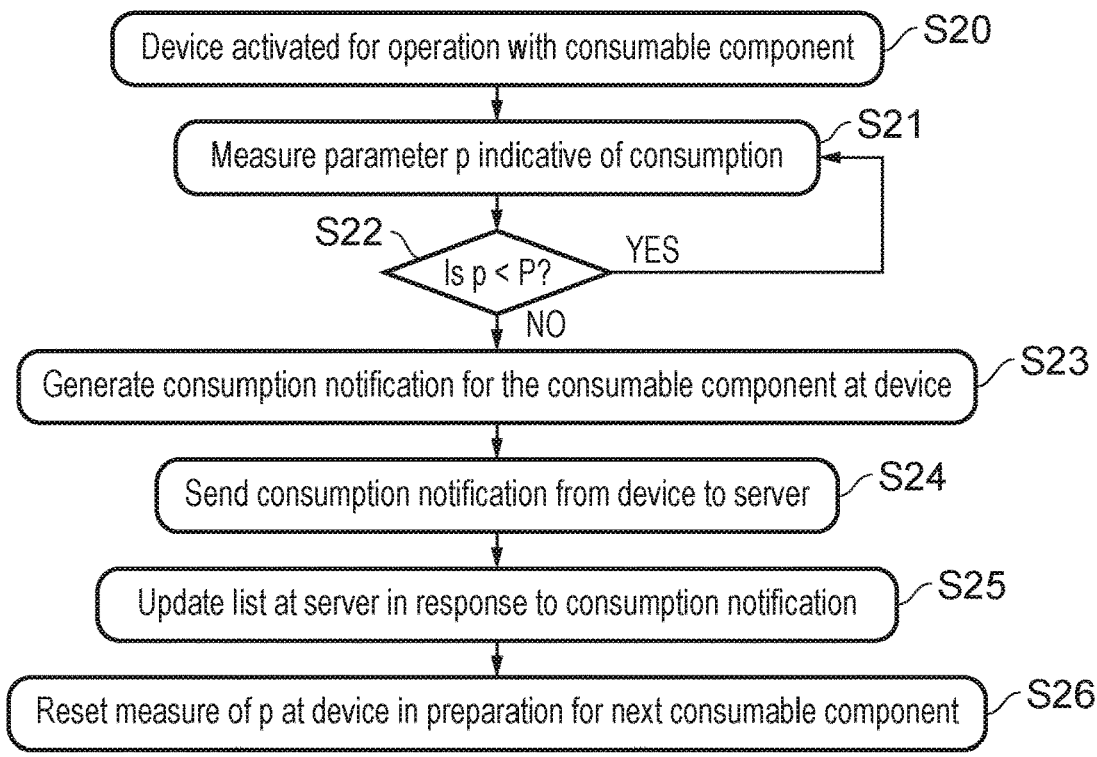
FIG. 6 shows a flow chart of steps in an example method for maintaining a list of identifiers of consumable components according to the present disclosure.

Once this state has been reached, the FIG. 5 method allows a reset of unauthorized usage of the aerosol provision system. The method moves to S15b, in which the processor monitors for a condition that allows the count of unauthorized activations to be reset. This may be any of the conditions noted above such as measuring time, counting authorized activations, or receiving a permission message, or other conditions. If in S16b, the condition is not found to be satisfied, the method continues monitoring in S15b. If in S16b the condition is determined to have been satisfied, the method moves to 517b, in which the count of unauthorized activations is either reset to zero, so that n=0, or is otherwise reduced below the maximum permitted number so that n<N by some amount. The device will then be able to activate for use with a next consumable component in the event that it is not possible to obtain an authorization response as in S11.

The list of authorized consumable components held by the server may be maintained in an up-to-date condition that accurately or reasonably accurately reflects the identities of the consumable components that have been manufactured and/or made available to users, but not yet consumed. This can be done by periodically replacing the entire list with a new list, and/or by adding and removing individual identifiers or groups of identifiers to and from the list.

Adding an identifier allocated to a consumable component into the list can be considered to be authorization of that component, or group of components in the case of a shared identifier. The addition and hence authorization may be performed concurrently or relatively concurrently with manufacture of the consumable components. The manufacturer may maintain a local list of all identifiers allocated to consumable components (where allocation is the providing of the corresponding identification information into the consumable component, as explained above), and then provides this local list to be added to the list held by the server on a periodic basis, such as each day or each week. The addition may be made by the manufacturer or by another approved party. Alternatively, the local list may be kept by the manufacturer and released for addition to the server list when the consumable components are distributed for supply to users or retail outlets. As a further alternative, consumable components may be individually (or in packs) authorized at the point of sale. The retailer may communicate the identification information for inclusion in the server list when the consumable component is sold or otherwise passed to a user. As an example, the packaging of the consumable may include a scannable code (barcode, QR code) corresponding to the identification information of the consumable, which is scanned by the retailer and transmitted to an authorized party responsible for maintaining the list at the server, or transmitted directly to the server as an update message, in response to which the server updates its list.

The list at the server can also be maintained up-to-date with regard to consumable components that have been used or consumed, or expected to have been used or consumed. In a simple example, the server list can include, for each identifier, the date when the identifier was added to the list. Then, an identifier can be maintained on the list for a given time period, and removed at the expiry of that time period. Depending on the expected turnover of consumable components, and known shelf-life beyond which the aerosolizable substrate material may become less suitable for consumption, the time period may be set to be, for example, six months, twelve months, eighteen months, or two years, or other or longer time periods.

Additionally or alternatively, the removal of identifiers from the list may follow a more active approach. Specifically, following activation (authorized or unauthorized) of a consumable component, the processor of the device may monitor one or more parameters to determine or estimate when the consumable component has been fully consumed, such as when the aerosolizable substrate material has been fully used up, or been used up to a maximum desirable level (having regard to any subsequent anticipated decrease in vapor quality, for example).

The parameter may be the number of inhalations on the aerosol provision system since the most recent activation, for example. The processor can be provided with a number of permissible inhalations for a given type or model of consumable component, having regard to the quantity of aerosolizable substrate material included in that component and the rate at which it is aerosolized, the number being that at which it is expected that most or all of the used substrate material will have been consumed. The processor keeps a count of the number of inhalations, and when the permissible number is reached, the processor generates a message to send to the server via the communications network. The message is a consumption notification that includes the identifier of the consumable component, and is configured to instruct the server to remove that identifier from the list, or otherwise update the list to indicate that the identifier is no longer authorized or available for use. It is appropriate for the server to action the removal or update upon receipt of the consumption notification if the identifier is unique to the consumable component. In examples where the identifier is allocated to a group or batch of consumable components sharing one or more characteristics, the server may store information regarding the quantity of consumable components in the group, and only action the removal when a number of consumption notifications matching the stored quantity has been received. If this condition is not met after a predetermined time period, the identifier may be removed from the list anyway, to account for any unsold or lost or defective consumable components that will never be activated for use.

Alternatively or additionally, the parameter may be time since the most recent activation, for example. An average, typical or expected duration of time to consume a given design of consumable component may be determined, and provided to the device. When the device recognizes the identifier, it can measure or monitor elapsed time from activation of the consumable component. When the elapsed time reaches the determined duration, the processor can generate a consumption notification and transmit it to the server via the network. The determined duration may be an amount of real time from activation, or may be an accumulated total of time periods of aerosol generation, such as durations of operation of the atomizer.

Other techniques for monitoring or estimating aerosolizable substrate consumption or otherwise estimating or ascertaining consumption of a consumable component may also be used to trigger the sending of a consumption notification from the device to the server.

Removal of identifiers corresponding to consumed and/or old consumable components from the server list can inhibit the use of expired identifiers by the manufacturers or distributers of counterfeit consumable components. This can improve safety by reducing the ability of devices to enable activation of counterfeit or otherwise unauthorized consumable components. Nevertheless, identifiers previously removed from the server list may be released for allocation to new consumable components by approved manufacturers after some period of time if desired, to maintain the pool of available identifiers.

The list of authorized consumable components held by the server may take any form or configuration that can be interrogated, searched or otherwise scanned to determine the presence or absence of a particular identifier designated in a received message requesting authorization of that identifier. Similarly, the identifiers may take any form or configuration that enables holding of the identifiers in such a list and the searching of the list for a designated identifier. The list may be considered as a database in some examples, and may include other information, such as the date when an identifier is added to the list, an indication of any previous inclusion of an identifier in the list, perhaps including dates, to facilitate possible reuse of identifiers, indicators of whether a identifier is allocated to an individual consumable component or to a group of components, and a description of the nature or characteristics of the corresponding components.

FIG. 6 shows a flow chart of an example method for maintaining a list of identifiers at the server in response to consumption of consumable components.

In S20, the device is activated for operation with a consumable component. This may be via S10*a* of FIG. 4 or S14*a* of FIG. 5, for example. In S21, the processor then begins to monitor, measure or otherwise record a parameter p which is considered to indicate or provide some measure of the consumption of a consumable component. As noted above, this may be counting a number of inhalations on the aerosol provision system, or counting a number of vaporizer uses, or measuring a cumulative time of vaporizer use, or measuring a total absolute time since activation, or any other measure that represents when a consumable component can be deemed to have been used up or otherwise be unsuitable for further use.

In S22 the measured level of the parameter p is tested against a preset total P which represents a value of the parameter considered to correspond to the consumable component having been consumed or otherwise have become unusable. If p is found to be less than P, the consumable component is considered still usable, and operation with the device carries on. The parameter continues to be measured in S21. If p is found to be equal to or greater than P (in other words, the test of is $p<P$ is answered as no), the method passes to S23 in which the device processor creates a consumption notification for the now-consumed consumable component as described above. In S24, the consumption notification is sent from the device to the server, and in S25, the server list of identifiers is updated to reflect the content of the consumption notification. In S26, the measure of p at the device processor is reset, ready for p to be measured for a next consumable component following activation in S20.

The examples described thus far have included a single identifier in an authorization query, derived from the identification information obtained from a consumable component engaged with the device at that time. However, the disclosure is not limited in this regard, and in some examples, an authorization query may include more than one identifier. To achieve this, the processor can store identification information obtained from more than one consumable component, or identifiers configured from that identification information, in local memory included in the device. Then, the processor constructs an authorization query that includes at least two identifiers (plurality of identifiers) corresponding to this identification information of more than one consumable component (plurality of consumables), and sends the authorization query to the remote server. The remote server interrogates its list of authorized identifiers for each of the identifiers in the authorization query, and formulates an authorization response including an indication for each identifier to show that it is or is not comprised in the list. The response might include a positive or negative indication for every identifier in the query. Alternatively, it might include an indication only for the identifiers which are on the list, so that the processor of the device interprets the absence of an indication for any identifier as notification that that particular identifier is not included in the list of authorized identifiers. Alternatively, the server might send a separate authorization response for each identifier, positive or negative as appropriate, or a separate authorization response only for each identifier found on the list.

The processor is then able to, if appropriate, cause an authorized activation for the present consumable component if there is a positive indication of its identifier in the authorization response. The indications for all other identifiers covered by the authorization query and the corresponding authorization response can be used by the processor to retroactively designate previously engaged and/or activated consumable components as authorized or unauthorized. This information can be used to update the count of unauthorized device activations, maintained as described with reference to FIG. 5. The count can be reduced if a previous unauthorized activation proves to have been performed with an authorized consumable.

This arrangement allows the bulk handling of authorizations. It may be useful in circumstances when the ability of the device to communicate with the server is compromised for a significant time period. The device can stock-pile identifiers for all connected consumable components until the communications network becomes accessible again, and then seek and obtain authorization information for all the consumable components with a single authorization query and a single authorization response.

As an alternative, the use of an authorization request covering a plurality of identifiers might be used as a default mode of operation of the device, to reduce the number of communications. A newly coupled consumable component can have its identification information obtained, and be activated for operation without the need for any authorization query and response procedure (i.e. the identifier of the consumable is not yet identified as authorized or unauthorized). This activation can be logged as an unauthorized activation to obtain a count n such as has been described with regard to FIG. 5. After a number of consumables have been used in this way, a bulk authorization response can be formulated and sent to the server. The information in the authorization response received from the server can be used to update the count of unauthorized activations, by reducing the count n by 1 for every identifier which the authorization response indicates as being comprised in the list of authorized identifiers. For any identifiers for which no positive authorization response is obtained, the count n is not reduced.

In some implementations, the consumable component may be an element which is attachable to the device and is intended to be replaced periodically. For example, it is known in some aerosol provision systems which generate aerosol by heating tobacco (or other) material (tobacco heated product (THP) devices) for a tubular sleeve to be inserted into a heating chamber in the device, with rod-like heatable material consumables then being inserted into the sleeve for heating. In such a case, each pack of heatable material consumables (for example, a pack of twenty consumables) may be provided with such a sleeve. For such an arrangement, it may be easier and more cost-effective to provide an identifier on or in each sleeve (which then becomes the consumable component of the present disclosure) rather than on every heatable material consumable.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in the future.

The invention claimed is:

1. An aerosol provision device configured to couple to a consumable component, and comprising:
   a transceiver configured for connection of the aerosol provision device to a communications network; and
   a processor configured to:
   obtain identification information from a consumable component engaged with the device, the identification information being uniquely provided to the consumable component or to a group of consumable components to which the consumable component belongs,
   configure the identification information as an identifier for the consumable component,
   send, via the communications network, an authorization query including the identifier to a remote server holding a list of one or more authorized identifiers,
   receive, via the communications network, an authorization response to the authorization query from the remote server,
   identify the consumable component as authorized if the authorization response indicates that the identifier is comprised in the list of authorized identifiers, and
   activate the device for operation with the consumable component if the authorization response indicates that the identifier is not comprised in the list of authorized identifiers, where the operation is a generic operation.

2. The aerosol provision device according to claim 1, wherein the processor is further configured to activate the aerosol provision device for operation with the consumable component as an authorized activation if the authorization response indicates that the identifier is comprised in the list of authorized identifiers.

3. The aerosol provision device according to claim 1, wherein the processor is further configured to prevent operation of the aerosol provision device with the consumable component if the authorization response indicates that the identifier is not comprised in the list of authorized identifiers.

4. The aerosol provision device according to claim 1, wherein the processor is further configured to prevent operation of the aerosol provision device with the consumable component if no authorization response is received to the authorization query.

5. The aerosol provision device according to claim 1, wherein the authorization query includes one or more additional identifiers for one or more additional consumable components previously engaged with the aerosol provision device, and wherein the processor is configured to identify the additional consumable components as authorized if the authorization response indicates that the additional identifiers are comprised in the list of authorized identifiers.

6. The aerosol provision device according to claim 1, wherein the processor is further configured to activate the aerosol provision device for operation with the consumable component if the identifier for the consumable component has not yet been indicated as not comprised in the list of authorized identifiers.

7. The aerosol provision device according to claim 1, wherein the processor is further configured to:
   determine an inability to obtain an authorization response from the remote server; and
   in the event of such an inability, identify the consumable component as unauthorized.

8. The aerosol provision device according to claim 7, wherein the processor is configured to, in the event of such an inability, activate the aerosol provision device for operation with the consumable component as an unauthorized activation if the current unauthorized activation plus any previous unauthorized activations does not exceed a predetermined allowable number of unauthorized activations.

9. The aerosol provision device according to claim 7, wherein an inability is determined when a failure of the communications network prevents the sending of an authorization query or the receiving of an authorization response.

10. The aerosol provision device according to claim 1, wherein the authorization query includes identifiers for a plurality of consumable components, and in which the processor is further configured, on the basis of the authorization response, to identify the respective consumable components as authorized or unauthorized.

11. The aerosol provision device according to claim 10, wherein the processor is further configured to determine a total number of unauthorized activations, and to prevent further unauthorized activations if the total number of unauthorized activations exceeds a predetermined allowable number of unauthorized activations.

12. The aerosol provision device according to claim 8, wherein the processor is configured to allow further unauthorized activations following an elapse of a predetermined time period after the predetermined allowable number of unauthorized activations has been allowed.

13. The aerosol provision device according to claim 8, wherein the processor is configured to allow further unauthorized activations in response to receiving a permission message via the network.

14. The aerosol provision device according to claim 1, wherein the processor is further configured to:
   determine consumption of the consumable component following activation of operation of the aerosol provision device; and
   send, via the communication network, a consumption notification including the identifier to the remote server to instruct the remote server to remove the identifier from the list of authorized identifiers.

15. The aerosol provision device according to claim 8, wherein the processor determines consumption of the consumable component by monitoring a number of inhalations on the aerosol provision device until a predetermined number of inhalations has been made, or by monitoring duration of operation of an atomizer that generates aerosol from an aerosolizable substrate material in the consumable component until a predetermined total duration has elapsed.

16. The aerosol provision device according to claim 1, wherein the consumable component contains an aerosolizable substrate material.

17. A system comprising:
   an aerosol provision device according to claim 1; and
   a remote server for enabling operation of the aerosol provision device, wherein:
   the aerosol provision device is configured to engage with a consumable component, and the aerosol provision device comprises:
      a transceiver configured for connection of the aerosol provision device to a communications network; and
      a processor configured to:
         obtain identification information from a consumable component engaged with the aerosol provision device, the identification information being uniquely provided to the consumable component or to a group of consumable components to which the consumable component belongs,
      configure the identification information as an identifier for the consumable component,
      send, via the communications network, an authorization query including the identifier to the remote server,
      receive, via the communications network, an authorization response to the authorization query from the remote server,
      identify the consumable component as authorized if the authorization response indicates that the identifier is comprised in the list of authorized identifiers, and
      activate the device for operation with the consumable component if the authorization response indicates that the identifier is not comprised in the list of authorized identifiers, where the operation is a generic operation; and
   the server comprises:
   a transceiver configured for connection of the server to a communications network,
   memory storing a list of one or more authorized identifiers each comprising identification information unique to a consumable component or a group of consumable components and configured to engage with an aerosol provision device; and
   a processor configured to:
   receive from the aerosol provision device, via the communications network, an authorization query including an identifier,
   interrogate the list of authorized identifiers for the identifier, and
   send to the aerosol provision device, via the communications network, an authorization response indicating that the identifier is comprised in the list of authorized identifiers if the interrogation finds the identifier in the list of authorized identifiers.

18. The aerosol provision device of claim 1, wherein the generic operation comprises a reduced amount of heating or results in a reduced amount of vapor production than when the authorization response indicates that the identifier is comprised in the list of authorized identifiers.

19. The aerosol provision device of claim 1, wherein the generic operation comprises a reduced amount of heating than a higher level of heating employed when the authorization response indicates that the identifier is comprised in the list of authorized identifiers.

* * * * *